(12) United States Patent
Rossing et al.

(10) Patent No.: US 7,801,614 B2
(45) Date of Patent: *Sep. 21, 2010

(54) STIMULUS REGIMENS FOR CARDIOVASCULAR REFLEX CONTROL

(75) Inventors: Martin A. Rossing, Coon Rapids, MN (US); Robert S. Kieval, Medina, MN (US); David J. Serdar, Shorewood, MN (US); Bruce J. Persson, Albertville, MN (US)

(73) Assignee: CVRx, Inc., Minneapolis, MN (US)

( * ) Notice: Subject to any disclaimer, the term of this patent is extended or adjusted under 35 U.S.C. 154(b) by 809 days.

This patent is subject to a terminal disclaimer.

(21) Appl. No.: 11/552,005

(22) Filed: Oct. 23, 2006

(65) Prior Publication Data

US 2007/0049989 A1 Mar. 1, 2007

Related U.S. Application Data (63) Continuation of application No. 10/818,738, filed on Apr. 5, 2004, now Pat. No. 7,623,926, which is a continuation-in-part of application No. 09/964,079, filed on Sep. 26, 2001, now Pat. No. 6,985,774, which is a continuation-in-part of application No. 09/671,850, filed on Sep. 27, 2000, now Pat. No. 6,522,926, said application No. 10/818,738 is a continuation-in-part of application No. 09/963,777, filed on Sep. 26, 2001, now Pat. No. 7,158,832, which is a continuation-in-part of application No. 09/963,991, filed on Sep. 26, 2001, now Pat. No. 6,850,801.

(51) Int. Cl.
*A61N 1/18* (2006.01)
*A61N 1/32* (2006.01)

(52) U.S. Cl. .............................. 607/44; 607/70; 607/72

(58) Field of Classification Search .................. 607/44, 607/68–70, 72–74, 59
See application file for complete search history.

(56) References Cited

U.S. PATENT DOCUMENTS

| 3,522,811 A | 8/1970 | Schwartz et al. |
| 3,645,267 A | 2/1972 | Hagfors |

(Continued)

FOREIGN PATENT DOCUMENTS

WO    WO 97/18856    5/1997

(Continued)

OTHER PUBLICATIONS

Bolter et al. "Influence of cervical sympathetic nerve stimulation on carotid sinus baroreceptor afferents," Experientia. Nov. 15, 1980;36(11):1301-1302.

(Continued)

*Primary Examiner*—Carl H. Layno
*Assistant Examiner*—Tammie K Heller
(74) *Attorney, Agent, or Firm*—Patterson Thuente Christensen Pedersen, P.A.

(57) ABSTRACT

Baroreflex activation is achieved by providing suitable control signals to a baroreflex activation device. A method comprises establishing a therapy interval (possibly on the order of minutes to hours, or possibly of indefinite duration), within the therapy interval, establishing a plurality of dose intervals, and generating an electrical output signal. The electrical output signal has a time dependence such that the average electrical power applied to the baroreflex activation device differs between first and second portions of at least some dose intervals. Another method comprises establishing a series of therapy interval portions, during at least some therapy intervals, establishing a plurality of burst intervals (perhaps having durations commensurate with an interval between heartbeats), and generating an electrical output signal. The electrical output signal has a time dependence such that the average electrical power applied to the baroreflex activation device differs between first and second portions of the therapy intervals and also differs between first and second portions of at least some burst intervals.

3 Claims, 5 Drawing Sheets

U.S. PATENT DOCUMENTS

| | | | |
|---|---|---|---|
| 3,650,277 A | 3/1972 | Sjostrand et al. | |
| 3,835,864 A | 9/1974 | Rasor et al. | |
| 3,870,051 A | 3/1975 | Brindley | |
| 3,943,936 A | 3/1976 | Rasor et al. | |
| 4,014,318 A | 3/1977 | Dockum et al. | |
| RE30,366 E | 8/1980 | Rasor et al. | |
| 4,256,094 A | 3/1981 | Kapp et al. | |
| 4,323,073 A | 4/1982 | Ferris | |
| 4,331,157 A | 5/1982 | Keller, Jr. et al. | |
| 4,481,953 A | 11/1984 | Gold et al. | |
| 4,525,074 A | 6/1985 | Murakami | |
| 4,531,943 A | 7/1985 | Van Tassel et al. | |
| 4,551,862 A | 11/1985 | Haber | |
| 4,573,481 A | 3/1986 | Bullara | |
| 4,586,501 A | 5/1986 | Claracq | |
| 4,590,946 A | 5/1986 | Loeb | |
| 4,640,286 A | 2/1987 | Thomson | |
| 4,641,664 A | 2/1987 | Botvidsson | |
| 4,664,120 A | 5/1987 | Hess | |
| 4,682,583 A | 7/1987 | Burton et al. | |
| 4,702,254 A | 10/1987 | Zabara | |
| 4,709,690 A | 12/1987 | Haber | |
| 4,711,251 A | 12/1987 | Stokes | |
| 4,719,921 A | 1/1988 | Chirife | |
| 4,739,762 A | 4/1988 | Palmaz | |
| 4,762,130 A | 8/1988 | Fogarty et al. | |
| 4,762,820 A | 8/1988 | Gavras | |
| 4,770,177 A | 9/1988 | Schroeppel | |
| 4,791,931 A | 12/1988 | Slate | |
| 4,800,882 A | 1/1989 | Gianturco | |
| 4,803,988 A | 2/1989 | Thomson | |
| 4,813,418 A | 3/1989 | Harris | |
| 4,825,871 A | 5/1989 | Cansell | |
| 4,828,544 A | 5/1989 | Lane et al. | |
| 4,830,003 A | 5/1989 | Wolff et al. | |
| 4,860,751 A | 8/1989 | Callaghan | |
| 4,867,164 A | 9/1989 | Zabara | |
| 4,881,939 A | 11/1989 | Newman | |
| 4,886,062 A | 12/1989 | Wiktor | |
| 4,887,608 A | 12/1989 | Mohl et al. | |
| 4,917,092 A | 4/1990 | Todd et al. | |
| 4,960,133 A | 10/1990 | Hewson | |
| 4,969,458 A | 11/1990 | Wiktor | |
| 4,972,848 A | 11/1990 | Di Domenico et al. | |
| 4,987,897 A | 1/1991 | Funke | |
| 5,025,807 A | 6/1991 | Zabara | |
| 5,040,533 A | 8/1991 | Fearnot | |
| 5,078,736 A | 1/1992 | Behl | |
| 5,086,787 A | 2/1992 | Grandjean et al. | |
| 5,092,332 A | 3/1992 | Lee et al. | |
| 5,113,859 A | 5/1992 | Funke | |
| 5,113,869 A | 5/1992 | Nappholz et al. | |
| 5,117,826 A | 6/1992 | Bartelt et al. | |
| 5,134,997 A | 8/1992 | Bennett et al. | |
| 5,154,170 A | 10/1992 | Bennett et al. | |
| 5,154,182 A | 10/1992 | Moaddeb | |
| 5,158,078 A | 10/1992 | Bennett et al. | |
| 5,170,802 A | 12/1992 | Mehra | |
| 5,181,911 A | 1/1993 | Shturman | |
| 5,199,428 A | 4/1993 | Obel et al. | |
| 5,203,326 A | 4/1993 | Collins | |
| 5,215,089 A | 6/1993 | Baker, Jr. | |
| 5,222,971 A | 6/1993 | Willard et al. | |
| 5,224,491 A | 7/1993 | Mehra | |
| 5,259,394 A | 11/1993 | Bens | |
| 5,265,608 A | 11/1993 | Lee et al. | |
| 5,282,468 A | 2/1994 | Klepinski | |
| 5,295,959 A | 3/1994 | Gurbel et al. | |
| 5,299,569 A | 4/1994 | Wernicke et al. | |
| 5,304,206 A | 4/1994 | Baker, Jr. et al. | |
| 5,314,453 A | 5/1994 | Jeutter | |
| 5,318,592 A | 6/1994 | Schaldach | |
| 5,324,310 A | 6/1994 | Greeninger et al. | |
| 5,324,325 A | 6/1994 | Moaddeb | |
| 5,330,507 A | 7/1994 | Schwartz | |
| 5,330,515 A | 7/1994 | Rutecki et al. | |
| 5,331,966 A | 7/1994 | Bennett et al. | |
| 5,351,394 A | 10/1994 | Weinberg | |
| 5,387,234 A | 2/1995 | Hirschberg | |
| 5,408,744 A | 4/1995 | Gates | |
| 5,411,540 A | 5/1995 | Edell et al. | |
| 5,458,626 A | 10/1995 | Krause | |
| 5,509,888 A | 4/1996 | Miller | |
| 5,522,854 A | 6/1996 | Ideker et al. | |
| 5,522,874 A | 6/1996 | Gates | |
| 5,529,067 A | 6/1996 | Larsen et al. | |
| 5,531,779 A | 7/1996 | Dahl et al. | |
| 5,535,752 A | 7/1996 | Halperin et al. | |
| 5,540,734 A | 7/1996 | Zabara | |
| 5,540,735 A | 7/1996 | Wingrove | |
| 5,545,132 A | 8/1996 | Fagan et al. | |
| 5,545,202 A | 8/1996 | Dahl et al. | |
| 5,571,150 A | 11/1996 | Wernicke et al. | |
| 5,575,809 A | 11/1996 | Sasaki | |
| 5,578,061 A | 11/1996 | Stroetmann et al. | |
| 5,634,878 A | 6/1997 | Grundei et al. | |
| 5,643,330 A | 7/1997 | Holsheimer et al. | |
| 5,651,378 A | 7/1997 | Matheny et al. | |
| 5,690,681 A | 11/1997 | Geddes et al. | |
| 5,692,882 A | 12/1997 | Bozeman, Jr. et al. | |
| 5,695,468 A | 12/1997 | Lafontaine et al. | |
| 5,700,282 A | 12/1997 | Zabara | |
| 5,707,400 A | 1/1998 | Terry, Jr. et al. | |
| 5,715,837 A | 2/1998 | Chen | |
| 5,725,471 A | 3/1998 | Davey et al. | |
| 5,725,563 A | 3/1998 | Klotz | |
| 5,727,558 A | 3/1998 | Hakki et al. | |
| 5,741,316 A | 4/1998 | Chen et al. | |
| 5,766,236 A | 6/1998 | Detty et al. | |
| 5,766,527 A | 6/1998 | Schildgen et al. | |
| 5,776,178 A | 7/1998 | Pohndorf et al. | |
| 5,800,464 A | 9/1998 | Kieval | |
| 5,807,258 A | 9/1998 | Cimochowski et al. | |
| 5,810,735 A | 9/1998 | Halperin et al. | |
| 5,814,079 A | 9/1998 | Kieval | |
| 5,824,021 A | 10/1998 | Rise | |
| 5,853,652 A | 12/1998 | Schildgen et al. | |
| 5,861,012 A | 1/1999 | Stroebel | |
| 5,861,015 A | 1/1999 | Benja-Athon | |
| 5,876,422 A | 3/1999 | van Groeningen | |
| 5,891,181 A | 4/1999 | Zhu | |
| 5,904,708 A | 5/1999 | Goedeke | |
| 5,913,876 A | 6/1999 | Taylor et al. | |
| 5,916,239 A | 6/1999 | Geddes et al. | |
| 5,919,220 A | 7/1999 | Stieglitz et al. | |
| 5,928,272 A | 7/1999 | Adkins et al. | |
| 5,938,596 A | 8/1999 | Woloszki et al. | |
| 5,967,986 A | 10/1999 | Cimochowski et al. | |
| 5,967,989 A | 10/1999 | Cimochowski et al. | |
| 5,987,352 A | 11/1999 | Klein et al. | |
| 5,987,746 A | 11/1999 | Williams | |
| 5,989,230 A | 11/1999 | Frassica | |
| 5,991,667 A | 11/1999 | Feith | |
| 6,006,134 A | 12/1999 | Hill et al. | |
| 6,016,449 A | 1/2000 | Fischell et al. | |
| 6,023,642 A | 2/2000 | Shealy et al. | |
| 6,050,952 A | 4/2000 | Hakki et al. | |
| 6,052,623 A | 4/2000 | Fenner et al. | |
| 6,058,331 A | 5/2000 | King | |
| 6,061,596 A | 5/2000 | Richmond et al. | |
| 6,073,048 A | 6/2000 | Kieval et al. | |
| 6,077,227 A | 6/2000 | Miesel et al. | |
| 6,077,298 A | 6/2000 | Tu et al. | |
| 6,106,477 A | 8/2000 | Miesel et al. | |

| | | |
|---|---|---|
| 6,161,029 A | 12/2000 | Spreigl et al. |
| 6,178,349 B1 | 1/2001 | Kieval |
| 6,208,894 B1 | 3/2001 | Schulman et al. |
| 6,231,516 B1 | 5/2001 | Keilman et al. |
| 6,253,110 B1 | 6/2001 | Brabec et al. |
| 6,255,296 B1 | 7/2001 | Daniels |
| 6,292,695 B1 | 9/2001 | Webster, Jr. et al. |
| 6,292,703 B1 | 9/2001 | Meier et al. |
| 6,438,428 B1 | 8/2002 | Axelgaard et al. |
| 6,522,926 B1 | 2/2003 | Kieval et al. |
| 6,564,101 B1 | 5/2003 | Zikria |
| 6,666,826 B2 | 12/2003 | Salo et al. |
| 6,701,186 B2 | 3/2004 | Spinelli et al. |
| 6,704,598 B2 | 3/2004 | Ding et al. |
| 6,748,272 B2 | 6/2004 | Carlson et al. |
| 6,766,189 B2 | 7/2004 | Yu et al. |
| 6,768,923 B2 | 7/2004 | Ding et al. |
| 6,779,257 B2 | 8/2004 | Kiepen et al. |
| 6,850,801 B2 | 2/2005 | Kieval et al. |
| 6,985,774 B2 | 1/2006 | Kieval et al. |
| 7,155,284 B1 | 12/2006 | Whitehurst et al. |
| 2001/0020177 A1 | 9/2001 | Gruzdowich et al. |
| 2002/0005982 A1 | 1/2002 | Borlinghaus |
| 2002/0103516 A1 | 8/2002 | Patwardhan et al. |
| 2002/0151051 A1 | 10/2002 | Li |
| 2003/0040785 A1 | 2/2003 | Maschino et al. |
| 2003/0060848 A1 | 3/2003 | Kieval et al. |
| 2003/0060857 A1 | 3/2003 | Perrson et al. |
| 2003/0060858 A1 | 3/2003 | Kieval et al. |
| 2004/0010303 A1 | 1/2004 | Bolea et al. |
| 2004/0019364 A1 | 1/2004 | Kieval et al. |
| 2004/0062852 A1 | 4/2004 | Schroeder et al. |
| 2004/0102818 A1 | 5/2004 | Hakky et al. |
| 2004/0193231 A1 | 9/2004 | David et al. |
| 2004/0249416 A1 | 12/2004 | Yun et al. |
| 2004/0249417 A1 | 12/2004 | Ransbury et al. |
| 2004/0254616 A1 | 12/2004 | Rossing et al. |
| 2005/0021092 A1 | 1/2005 | Yun et al. |
| 2005/0143779 A1 | 6/2005 | Libbus |
| 2005/0143785 A1 | 6/2005 | Libbus |
| 2005/0149126 A1 | 7/2005 | Libbus |
| 2005/0149127 A1 | 7/2005 | Libbus |
| 2005/0149128 A1 | 7/2005 | Heil et al. |
| 2005/0149129 A1 | 7/2005 | Libbus et al. |
| 2005/0149130 A1 | 7/2005 | Libbus |
| 2005/0149131 A1 | 7/2005 | Libbus et al. |
| 2005/0149132 A1 | 7/2005 | Libbus |
| 2005/0149133 A1 | 7/2005 | Libbus et al. |
| 2005/0149143 A1 | 7/2005 | Libbus et al. |
| 2005/0149155 A1 | 7/2005 | Scheiner et al. |
| 2005/0149156 A1 | 7/2005 | Libbus et al. |
| 2005/0182468 A1 | 8/2005 | Hunter et al. |
| 2006/0224222 A1 | 10/2006 | Bradley et al. |

FOREIGN PATENT DOCUMENTS

| | | |
|---|---|---|
| WO | WO 98/02209 | 1/1998 |
| WO | WO 99/26530 | 6/1999 |
| WO | WO 99/42039 | 8/1999 |
| WO | WO 99/42176 | 8/1999 |
| WO | WO 99/51286 A1 | 10/1999 |
| WO | WO 00/16686 | 3/2000 |
| WO | WO 01/00273 | 1/2001 |
| WO | WO 02/26314 | 4/2002 |
| WO | WO 02/070039 | 9/2002 |
| WO | WO 03/076008 | 9/2003 |

OTHER PUBLICATIONS

Fan et al., "Graded and dynamic reflex summation of myelinated and unmyelinated rat aortic baroreceptors," Am J Physiol Regul Integr Comp Physiol, Sep. 1999; 277(3): R748-R756.

Bilgutay et al., "Baropacing, a New Concept in the Treatment of Hypertension," from *Baroreceptors and Hypertension Proceedings of an International Symposium*, (Nov. 1965), p. 425-437.

Bilgutay et al., "Surgical Treatment of Hypertension with Reference to Baropacing," *Am. J of Cardiology*, vol. 17, (May 1966), pp. 663-667.

Bock et al, "Fine Structure of Baroreceptor Terminals in the Carotid Sinus of Guinea Pigs and Mice," *Cell & Tissue Research*, vol. 170, (1976), pp. 95-112.

Brattstrom, "Influence of Continuous and Intermittent (R-Wave Triggered) Electrical Stimulation of the Carotid Sinus Nerve on the Static Characteristic of the Circularoty Regulator," *Experientia*, vol. 28, (1972), pp. 414-416.

Coleridge et al., "Impulse in Slowly Conducting Vagal Fibers from Afferent Endings in the Veins, Atria, and Arteries of Dogs and Cats," *Circ. Res.*, vol. 33, (Jul. 1973), pp. 87-97.

Correspondence, *The New England of Journal of Medicine*, vol. 281, No. 2., (Jul. 3, 1969), p. 103.

Eckberg et al., "Baroflex anatomy" In: Monographs of the Physiological Society (43): *Human Baroreflex in Health and Disease*. Oxford, UK: Clarendon Press, (1992), pp. 19-30.

Goldberger et al., "New Technique for Vagal Nerve Stimulation," *Journal of Neuroscience Methods*, vol. 91, (1999), pp. 109-114.

Hainsworth, "Cardiovascular Reflexes From Ventricular & Coronary Receptors," *Adv. Exp. Med. Biol.*, vol. 381, (1999), pp. 157-174.

Harrison, "Carotid Sinus Stimulation for the Treatment of Angina Pectoris," *Official Journal of the Calif. Medical Assoc.*, vol. 112, No. 3, (Mar. 1970), pp. 78-79.

Itoh, "Studies on the Carotid Body & the Carotid Sinus Effects on the Heart by Electrical Stimulation of the Carotid Sinus Wall," *Jap. Heart J.*, vol. 13, No. 2, (Mar. 1972), pp. 136-149.

Kostreva et al., "Hepatic Vein, Hapatic Parenchymal, and Inferior Vena Caval Mechanoreceptors with Phrenic Afferents," *Am. J. Physiol.*, vol. 265, 1993, pp. G15-G20.

Krauhs, "Structure of Rat Aortic Baroreceptors & Their Relationship to Connective Tissue," *Journal of Neurocytology*, vol. 8, (1979), pp. 401-414.

Lindblad et al., "Circulatory Effects of Carotid Sinus Stimulation & Changes in Blood Volume Distribution in Hypertensive Man", *Acta. Physiol. Scand.*, vol. 111, (Mar. 1981), pp. 299-306.

Mifflin et al., "Rapid Resetting of Low Pressure Vagal Receptors in the Superior Vena Cava of the Rat," *Circ. Res*, vol. 51 ,(1982) pp. 241-249.

Neufeld, "Stimulation of the Carotid Baroreceptors Using a Radio-Frequency Method," *Israel J. Med. Sci.*, vol. 1, No. 4, (Jul. 1965), pp. 630-632.

Peters et al., "Cardiovascular response to time delays of electrocardiogram-coupled electrical stimulation of carotid sinus nerves in dogs," *Journal of the Autonomic Nervous Systems*, vol. 25, (1988), pp. 173-180.

Peters et al., "The Principle of Electrical Carotid Sinus Nerve Stimulation: A Nerve Pacemaker System for Angina Pectoris and Hypertension Therapy," *Annals of Biomedical Engineering*, vol. 8, (1980), pp. 445-458.

Rau et al., "Psychophysiology of Arterial Baroreceptors and the Etiology of Hypertension," *Biol. Psychol.*, vol. 57, (2001), pp. 179-201.

Reich, "Implantation of a Carotid Sinus Nerve Stimulator," *AORN Journal*, (Dec. 1969.), pp. 53-56.

Richter et al., "The Course of Inhibition of Sympathetic Activity during Various Patterns of Carotid Sinus Nerve Stimulation," *Pflugers Arch.*, vol. 317, (1970), pp. 110-123.

Schauerte et al., "Transvenous parasympathetic nerve stimulation in the inferior vena cava and atrioventricular conduction," *J. Cardiovasc. Electrophysiol.*, (Jan. 2000), 1 page.

Sedin, "Responses of the Cardiovascular System to Carotid Sinus Nerve Stimulation," *Upsala J Med Sci*, Vo. 81, (1976), pp. 1-17.

Silber, "The treatment of Heart Disease," *Heart Disease*, 2.sup.nd Edition, MacMillan Publishing Co., (1987), p. 1642.

Solti, "Baropacing of the Carotid Sinus Nerve for Treatment of Intractable Hypertension," *Zeitschrift Fur Kardiologie*, band 64, Heft 4, (1975), pp. 368-374.

Solti, "The Haemodynamic Basis of Anginal Relief Produced By Stimulation of the Carotid Sinus Nerve," *Acta Medica Academiae Scientiarum Hungaricae*, vol. 30 (1-2), (1973), pp. 61-65.

Stefanadis et al. "Non-invasive heat delivery to arterial stented segments in vivo: Effect of heat on neointimal hyperplasia (Abstr)" *J Am Coll Cardiol*, #1041-89, (Feb. 2000), p. 14A.

Tarver et al, "Clinical Experience with a Helical Bipolar Stimulating Lead," *PACE*, vol. 15, Part II, (Oct. 1992), pp. 1545-1556.

Tsakiris, "Changes in Left Ventricular End Diastolic Volume Pressure Relationship After Acute Cardiac Denervation," Abstracts of the 40th sup. Scientific Sessions, Supplement II to *Circulation*, vols. XXXV & XXXVI, (Oct. 1967), II-253, 1 sheet.

Warzel et. al., "Effects of Carotis Sinus Nerve Stimulation at Different Times in the Respiratory and Cardiac Cycles on Variability of Heart Rate and Blood Pressure of Normotensive and Renal Hypertensive Dogs," *Journal of the Autonomic Nervous System*, vol. 26, (1989) pp. 121-127.

Warzel et al., "The Effect of Time of Electrical Stimulation of the Carotid Sinus on the Amount of Reduction in Arterial Pressure," *Pflugers Arch.*, (1972) 337:39-44.

Yatteau, "Laryngospasm Induced by a Carotid-Sinus-Nerve Stimulator", N Engl J Med., No. 13, pp. 709-710, 1971.

Ebert et al., "Fentanyl-Diazepam Anesthesia with or without $N_2O$ Does Not Attenuate Cardiopulmonary Baroreflex-Mediated Vasoconstrictor Responses to Controlled Hypovolemia in Humans," Anesth Analg (1988) vol. 67, No. 6, pp. 548-554.

Abstracts of the 40th Scientific Sessions,' SupplementII to Circulation, vols. XXXV & XXXVI, Oct. 1967, II-253.

Kisch et al., "Baropacing of the Cartid Sinus Nerve for Treatment of Intractable Hypertension," Zeitschrift fur Kardiologic, (1975) Band 64, Heft 3, pp. 368-374.

Eckberg et al., "Baroreflex Anatomy," Human Baroreflexes in Health and Disease (1992) pp. 19-30.

Hainsworth, "Cardiovascular reflexes from ventricular and coronary receptors," Adv. Exp. Med. Biol. (1995) 381:247-74.

Harrison, California Medicine, The Western Journal of Medicine, (1970) vol. 112, No. 3 pp. 78-79.

Lindblad et al., "Circulatory Effects of Carotid Sinus Stimulation & Changes in Blood Volume Distribution in Hypertensive Man," Acta Physiologica Scandinavica (1981) vol. 111, No. 3, pp. 299-306.

Tarver et al., "Clinical Experience with a Helical Bipolar Stimulating Lead," PACE, (1992) vol. 15, Part II, pp. 1545-1556.

Bock et al., "Fine Structure of Baroreceptor Terminals in the Carotid Sinus of Guinea Pigs and Mice," Cell and Tissue Research (1976) pp. 95-112.

Reich, "Implantation of a carotid Sinus Nerve Stimulator," AORN Journal (1969) pp. 53-56.

Yatteau et al, "Laryngospasm Induced by a Carotid-Sinus-Nerve Stimulator," The New England Journal of Medicine, No. 13, pp. 709-710.

Goldberger et al., "New technique for vagal nerve stimulation," Journal of Neuroscience Methods (1999) pp. 109-114.

Stefanadis et al., "Non-Invasive Heat-Delivery to Arterial Stented Segments in Vivo: Effect of Heat on Intimal Hyperplasia," JACC (2000) p. 14A.

Neufeld et al., "Stimulation of the Carotid Barorectors Using a Radio-Frequency Method," Israel J. Med. Sci. (1965), vol. 1, No. 4, pp. 630-632.

Krauhs, "Structure of rat aortic baroreceptors and their relationship to connective tissue," Journal of Neurocytology (1979) pp. 401-414.

Itoh, "Studies on the Carotid Body and the Carotid Sinus Effects on the Heart by Electrical Stimulation of the Carotid Sinus Wall," Japanese Heart Journal (1972) vol. 13, No. 2, pp. 136-149.

Bilgutay et al., "Surgical Treatment of Hypertension with Reference to Baropacing," The American Journal of Cardiology (1966) vol. 17, pp. 663-667.

Solti et al., "The Haemodynamic Basis of Anginal Relief Produced by Stimulation of the Carotid Sinus Nerve," Acta Medica Academiae Scientiarum Hungaricae (1973) pp. 61-65.

Silber "The Treatment of Heart Disease," Heart Disease (1987), p. 1642.

Schauerte et al., "Transvenous parasympathetic nerve stimulation in the inferior vena cava and atrioventricular conduction," J. Cardiovascular Electrophysiol (2000) 1 page.

File Wrapper for U.S. Appl. No. 09/671,850 (U.S. Patent No. 6,522,926).

File Wrapper for U.S. Appl. No. 09/964,079 (U.S. Patent No. 6,985,774).

File Wrapper for U.S. Appl. No. 09/963,777 (U.S. Patent No. 7,158,832).

File Wrapper for U.S. Appl. No. 09/963,991 (U.S. Patent No. 6,850,801).

File Wrapper for U.S. Appl. No. 10/818,738 (U.S. Patent No. 7,623,926).

File Wrapper for U.S. Appl. No. 11/735,303 (U.S. Published Application No. 2007/0185543).

STIMULUS REGIMENS FOR CARDIOVASCULAR REFLEX CONTROL

This application is a continuation of U.S. patent application Ser. No. 10/818,738 filed on Apr. 5, 2004, now U.S. Pat. No. 7,623,926 issued Nov. 24, 2009, which is a continuation-in-part of (1) U.S. patent application Ser. No. 09/964,079, filed Sep. 26, 2001, now U.S. Pat. No. 6,985,774 issued Jan. 10, 2006, which is a continuation-in-part of U.S. patent application Ser. No. 09/671,850, filed Sep. 27, 2000, now U.S. Pat. No. 6,522,926 issued Feb. 18, 2003; of (2) U.S. patent application Ser. No. 09/963,777, filed Sep. 26, 2001, now U.S. Pat. No. 7,158,832 issued Jan. 2, 2007; and of (3) U.S. patent application Ser. No. 09/963,991, filed Sep. 26, 2001, now U.S. Pat. No. 6,850,801 issued Feb. 1, 2005, the full disclosures of which are incorporated herein by reference.

The disclosure of this application is related to and incorporates by reference the disclosures of U.S. patent application Ser. No. 10/402,911 filed Mar. 27, 2003 now U.S. Pat. No. 7,499,742 issued Mar. 3, 2009, and of U.S. patent application Ser. No. 10/402,303, filed on Mar. 27, 2003, now U.S. Pat. No. 7,616,997 issued Nov. 10, 2009.

BACKGROUND OF THE INVENTION

The present invention relates generally to medical devices and methods of use for the treatment and/or management of cardiovascular, neurological, and renal disorders, and more specifically to devices and methods for controlling the baroreflex system for the treatment and/or management of cardiovascular, neurological, and renal disorders and their underlying causes and conditions.

Hypertension, or high blood pressure, is a major cardiovascular disorder that is estimated to affect over 50 million people in the United Sates alone, and is a leading cause of heart failure and stroke. It is the primary cause of death in over 42,000 patients per year and is listed as a primary or contributing cause of death in over 200,000 patients per year in the United States alone. Hypertension occurs in part when the body's smaller blood vessels (arterioles) constrict, causing an increase in blood pressure. Because the blood vessels constrict, the heart must work harder to maintain blood flow at the higher pressures. Sustained hypertension may eventually result in damage to multiple body organs, including the kidneys, brain, eyes and other tissues, causing a variety of maladies associated therewith. The elevated blood pressure may also damage the lining of the blood vessels, accelerating the process of atherosclerosis and increasing the likelihood that a blood clot may develop. This could lead to a heart attack and/or stroke.

Sustained high blood pressure may eventually result in an enlarged and damaged heart (hypertrophy), which may lead to heart failure. Heart failure is the final common expression of a variety of cardiovascular disorders, including ischemic heart disease. It is characterized by an inability of the heart to pump enough blood to meet the body's needs and results in fatigue, reduced exercise capacity and poor survival. It is estimated that approximately 5,000,000 people in the United States suffer from heart failure, directly leading to 39,000 deaths per year and contributing to another 225,000 deaths per year.

A number of drug treatments have been proposed for the management of hypertension, heart failure, and other cardiovascular disorders. These include vasodilators to reduce the blood pressure and ease the workload of the heart, diuretics to reduce fluid overload, inhibitors and blocking agents of the body's neurohormonal responses, and other medicaments. Various surgical procedures have also been proposed for these maladies. For example, heart transplantation has been proposed for patients who suffer from severe, refractory heart failure. Alternatively, an implantable medical device such as a ventricular assist device (VAD) may be implanted in the chest to increase the pumping action of the heart. Alternatively, an intra-aortic balloon pump (IABP) may be used for maintaining heart function for short periods of time, but typically no longer than one month.

It has been known for decades that the wall of the carotid sinus, a structure at the bifurcation of the common carotid arteries, contains stretch receptors (baroreceptors) that are sensitive to the blood pressure. These receptors send signals via the carotid sinus nerve to the brain, which in turn regulates the cardiovascular system to maintain normal blood pressure (the baroreflex), in part through modulation of the sympathetic and/or parasympathetic nervous system. Electrical stimulation of the carotid sinus nerve (baropacing) has previously been proposed to reduce blood pressure and the workload of the heart in the treatment of high blood pressure and angina. For example, U.S. Pat. No. 6,073,048, issued Jun. 6, 2000 to Kieval et al. discloses a baroreflex modulation system and method for stimulating the baroreflex arc based on various cardiovascular and pulmonary parameters.

Although each of these alternative approaches is beneficial in some ways, each of the therapies has its own disadvantages. For example, drug therapy is often incompletely effective. Drugs often have unwanted side effects and may need to be given in complex regimens. These and other factors contribute to poor patient compliance with medical therapy. Drug therapy may also be expensive, adding to the health care costs associated with these disorders. Likewise, surgical approaches are very costly, may be associated with significant patient morbidity and mortality and may not alter the natural history of the disease. Baropacing also has not gained acceptance. Several problems with electrical carotid sinus nerve stimulation have been reported in the medical literature. These include the invasiveness of the surgical procedure to implant the nerve electrodes, and postoperative pain in the jaw, throat, face and head during stimulation. In addition, it has been noted that high voltages sometimes required for nerve stimulation may damage the carotid sinus nerves. Accordingly, there continues to be a substantial and long felt need for new devices and methods for treating and/or managing high blood pressure, heart failure, and their associated cardiovascular and nervous system disorders.

U.S. Pat. No. 6,522,926, issued Feb. 18, 2003 and assigned to the Assignee of the present application, describes a number of systems and methods intended to activate baroreceptors in the carotid sinus and elsewhere in order to induce the baroreflex. Numerous specific approaches are described, including the use of coil electrodes placed over the exterior of the carotid sinus near the carotid bifurcation.

SUMMARY OF THE INVENTION

The present invention provides techniques for activation of the baroreflex by providing suitable control signals to a baroreflex activation device. In this context, the term "baroreflex activation device" means a device that is located at or near a baroreceptor and/or nerve fibers that carry signals from the baroreceptor to the brain, and that when provided with such control signals, activates the baroreceptor and/or nerve fibers from the baroreceptor so as to activate the baroreflex system.

In general, cardiovascular receptors may be sensitive to pressure and/or mechanical deformation and are referred to as baroreceptors, mechanoreceptors, pressoreceptors, stretch receptors, and the like. For cardiovascular and renal therapies, the present invention is intended to activate or otherwise interact with any or all of these types of receptors and/or nerve fibers from the receptors so long as such activation or interaction results in modulation of the reflex control of the patient's circulation. While there may be small structural or anatomical differences among various receptors in the vasculature, for the purposes of the present invention, activation may be directed at any of these receptors and/or nerves from these receptors so long as they provide the desired effects. In particular, such receptors will provide afferent signals, i.e., signals to the brain, which provide the blood pressure and/or volume information to the brain. This allows the brain to cause "reflex" changes in the autonomic nervous system, which in turn modulate organ activity to maintain desired hemodynamics and organ perfusion. For convenience, the term "baroreceptor" will be used to refer to any or all of such receptors.

In one aspect of the present invention, a method of generating an electrical control signal for application to a baroreflex activation device comprises establishing a therapy interval (possibly on the order of minutes to hours, or possibly of indefinite duration), within the therapy interval, establishing a plurality of dose intervals, and generating an electrical output signal. The electrical output signal has a time dependence such that the average electrical power applied to the baroreflex activation device differs between first and second portions of at least some dose intervals.

More specifically, the control signal has a time dependence such that at least some dose intervals have a first portion characterized by an average electrical power, referred to as the first dose portion average power, and a second portion characterized by an average electrical power, referred to as the second dose portion average power, with the first dose portion average power being different from the second dose portion average power. In some embodiments, generating the electrical output signal comprises generating electrical pulses having one or more pulse characteristics (e.g., amplitudes, pulse widths, and separations) chosen to provide the desired time dependence of electrical power applied to the baroreflex activation device.

In some embodiments, the second dose portion average power is less than the first dose portion average power, and may be zero. In some embodiments, the first portion of at least one dose interval is characterized by a variation in first dose portion average power wherein the first dose portion average power near the center of the first portion of the dose interval is greater than the first dose portion average power near the beginning and end of the first portion of the dose interval. This may be in the form of an upwardly sloping ramp near the beginning of the first portion of the dose interval and a downwardly sloping ramp near the end of the first portion of the dose interval.

In some embodiments, the therapy interval is characterized by a variation in average power over a plurality of dose intervals, with the average power increasing during dose intervals near the beginning of the therapy interval. In some embodiments, the average electrical power differs between first and second portions of the therapy interval. More specifically, the therapy interval has a first portion characterized by an average electrical power, referred to as the first therapy portion average power, over a first plurality of dose intervals, and a second portion characterized by an average electrical power, referred to as the second therapy portion average power, over a second plurality of dose intervals, the first therapy portion average power being different from the second therapy portion average power. The second therapy portion average power may be less than the first therapy portion average power, and may be zero.

In some embodiments, the therapy interval is characterized by a variation in average power over a plurality of dose intervals, which variation may be characterized by an average power during dose intervals near the center of the first portion of the therapy interval that is greater than the average power during dose intervals near the beginning and end of the first portion of the therapy interval. The variation may include a generally linear region of positive slope over a first set of dose intervals near the beginning of the therapy interval, followed by a generally flat region over a second set of dose intervals and a generally linear region of negative slope over a third set of dose intervals. Other functional forms of increase and decrease are also possible.

In some embodiments, a first set of the electrical pulses is applied to a first of a plurality of baroreflex activation devices and a second set of the electrical pulses is applied to a second of the plurality of baroreflex activation devices. In some of these embodiments, the first and second sets of electrical pulses are interleaved at the dose interval level, while in others of these embodiments, the first and second sets of electrical pulses are interleaved at the individual pulse level. In the case where the plurality includes more than two baroreflex activation devices, one or both of the sets of pulses may be applied to more than one baroreflex activation device generally at the same time.

According to a further aspect of the present invention, a method of generating an electrical control signal for application to a baroreflex activation device comprises establishing a series of therapy interval portions, during at least some therapy intervals, establishing a plurality of burst intervals (perhaps having durations commensurate with an interval between heartbeats), and generating an electrical output signal. The electrical output signal has a time dependence such that the average electrical power applied to the baroreflex activation device differs between first and second portions of the therapy intervals and also differs between first and second portions of at least some burst intervals.

More specifically, the control signal has a time dependence such that (1) at least some therapy intervals have a first portion characterized by an average electrical power, referred to as the first therapy portion average power, and a second portion characterized by an average electrical power, referred to as the second therapy portion average power, with the first therapy portion average electrical power being different from the second therapy portion average electrical power, and (2) at least some burst intervals have a first portion characterized by an average electrical power, referred to as the first burst portion average power, and a second portion characterized by an average electrical power, referred to as the second burst portion average power, with the first burst portion average power being different from the second burst portion average power.

In some embodiments, the second therapy portion average power is less than the first therapy portion average power, and may be zero. In some embodiments, the second burst portion average power is less than the first burst portion average power, and may be zero. In some embodiments, generating the electrical output signal comprises generating electrical pulses having one or more pulse characteristics (e.g., amplitudes, pulse widths, and separations) chosen to provide the desired time dependence of electrical power applied to the baroreflex activation device.

In some embodiments, the average electrical power applied to the baroreflex activation device has a time dependence characterized by ascending ramps near the respective beginnings of the first portions of the therapy intervals and descending ramps near the respective ends of the first portions of the therapy intervals. In some embodiments, at least two successive therapy intervals are of equal length and have respective first portions that are of equal length.

In some embodiments, a first set of the electrical pulses is applied to a first of a plurality of baroreflex activation devices and a second set of the electrical pulses is applied to a second of the plurality of baroreflex activation devices. In some of these embodiments, the first and second sets of electrical pulses are interleaved at the burst interval level, while in others of these embodiments, the first and second sets of electrical pulses are interleaved at the individual pulse level.

According to a further aspect of the present invention, a method of generating an electrical control signal for application to a baroreflex activation device comprises establishing a therapy interval, within the therapy interval, establishing a plurality of dose intervals, within each dose interval, establishing a plurality of burst intervals, and generating an electrical output signal. The electrical output signal has a time dependence such that the average electrical power applied to the baroreflex activation device differs between first and second portions of the at least some dose intervals and also differs between first and second portions of at least some burst intervals.

More specifically, the control signal has a time dependence such that (1) at least some dose intervals have a first portion characterized by an average electrical power, referred to as the first dose portion average power, and a second portion characterized by an average electrical power, referred to as the second dose portion average power, with the first dose portion average power being different from the second dose portion average power, and (2) at least some burst intervals have a first portion characterized by a first average electrical power, referred to as the first burst portion average power, and a second portion characterized by a second average electrical power, referred to as the second burst portion average power, with the first burst portion average power being different from the second burst portion average power.

In some embodiments, the second dose portion average power is less than the first dose portion average power, and may be zero. In some embodiments, the second burst portion average power is less than the first burst portion average power, and may be zero. In some embodiments, generating the electrical output signal comprises generating electrical pulses having one or more pulse characteristics (e.g., amplitudes, pulse widths, and separations) chosen to provide the desired time dependence of electrical power applied to the baroreflex activation device.

In some embodiments, the therapy interval has a time dependence wherein a first portion is characterized by an average electrical power, referred to as the first therapy portion average power, over a first plurality of dose intervals, and a second portion characterized by an average electrical power, referred to as the second therapy portion average power, over a second plurality of dose intervals, with the first therapy portion average power being different from the second therapy portion average power. The second therapy portion average power may be less than the first portion average power, and may be zero.

In some embodiments, a first set of the electrical pulses is applied to a first of a plurality of baroreflex activation devices and a second set of the electrical pulses is applied to a second of the plurality of baroreflex activation devices. In some of these embodiments, the first and second sets of electrical pulses are interleaved at the dose interval level, in others of these embodiments, the first and second sets of electrical pulses are interleaved at the burst interval level, and in others of these embodiments, the first and second sets of electrical pulses are interleaved at the pulse level.

A further understanding of the nature and advantages of the present invention may be realized by reference to the remaining portions of the specification and the drawings.

DESCRIPTION OF SPECIFIC EMBODIMENTS

The following detailed description should be read with reference to the drawings in which similar elements in different drawings are numbered the same. The drawings, which are not necessarily to scale, depict illustrative embodiments and are not intended to limit the scope of the invention. The drawings illustrate the specific embodiment where one or more baroreflex activation devices are positioned near baroreceptors, but the invention is applicable to baroreflex activation devices that are positioned near nerve fibers that carry signals from the baroreceptor to the brain.

Anatomical Overview

Figure 1:
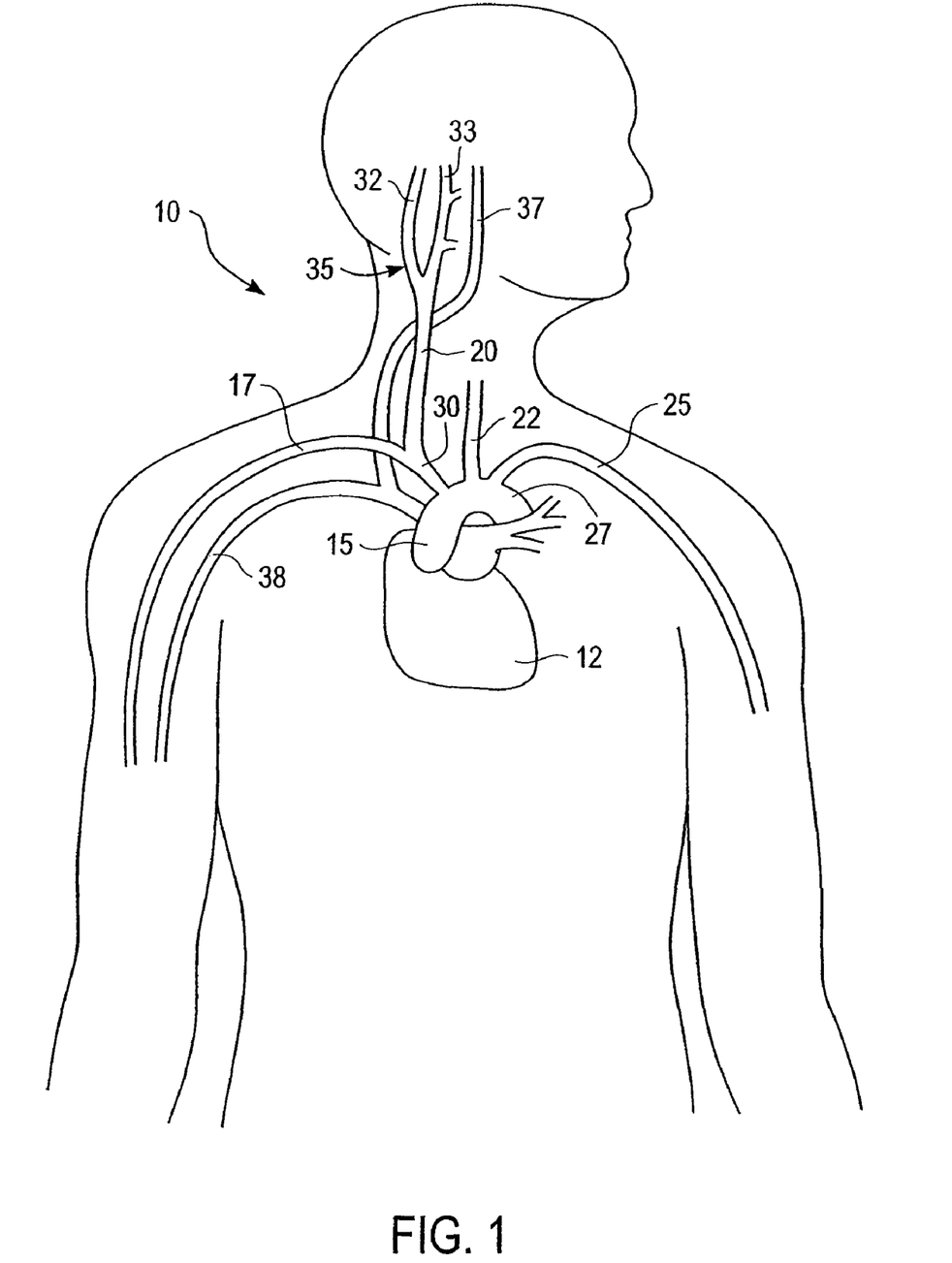
FIG. 1 is a schematic illustration of the chest and head regions of a human body showing the major arteries and veins and associated anatomy.

To better understand the present invention, it may be useful to explain some of the basic vascular anatomy associated with the cardiovascular system. FIG. 1 is a schematic illustration of the chest and head regions of a human body 10 showing some of the major arteries and veins of the cardiovascular system. The left ventricle of the heart 12 pumps oxygenated blood up into the aortic arch 15. The right subclavian artery 17, the right common carotid artery 20, the left common carotid artery 22, and the left subclavian artery 25 branch off the aortic arch 15 proximal of the descending thoracic aorta 27. Although relatively short, a distinct vascular segment referred to as the brachiocephalic artery 30 connects the right subclavian artery 17 and the right common carotid artery 20 to the aortic arch 15. The right carotid artery 20 bifurcates into the right external carotid artery 32 and the right internal carotid artery 33 at the right carotid sinus 35. Although not shown for purposes of clarity only, the left carotid artery 22 similarly bifurcates into the left external carotid artery and the left internal carotid artery at the left carotid sinus.

From the aortic arch 15, oxygenated blood flows into the carotid arteries 20/22 and the subclavian arteries 17/25. From the carotid arteries 20/22, oxygenated blood circulates through the head and cerebral vasculature and oxygen-depleted blood returns to the heart 12 by way of the jugular veins, of which only the right internal jugular vein 37 is shown for sake of clarity. From the subclavian arteries 17/25, oxygenated blood circulates through the upper peripheral vasculature and oxygen depleted blood returns to the heart by way of the subclavian veins, of which only the right subclavian vein 38 is shown, also for sake of clarity. The heart 12 pumps the oxygen depleted blood through the pulmonary system where it is re-oxygenated. The re-oxygenated blood returns to the heart 12 which pumps the re-oxygenated blood into the aortic arch as described above, and the cycle repeats.

Figure 2A:
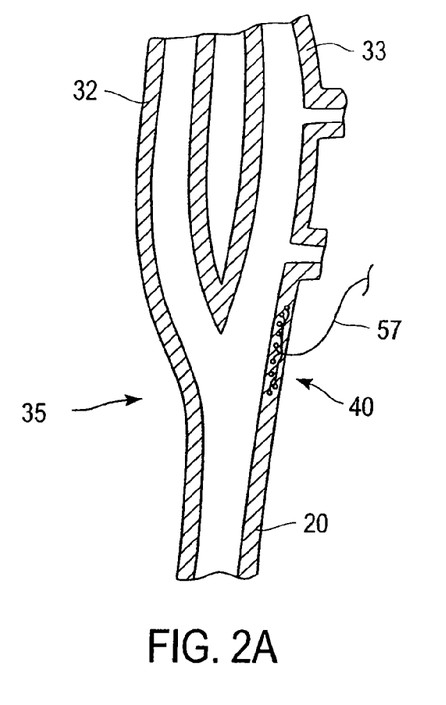
FIG. 2A is a cross-sectional schematic illustration of the carotid sinus and baroreceptors within the vascular wall.

FIG. 2A is a cross-sectional schematic illustration of the right carotid sinus 35 showing the presence of baroreceptors 40 within the vascular wall of the right common carotid artery 20 near the right carotid sinus 35. Baroreceptors are also present, for example, within the arterial walls of the aortic arch 15, the left common carotid artery 22 (near the left carotid sinus), subclavian arteries 17/25, and brachiocephalic artery 30. Baroreceptors 40 are a type of stretch receptor used by the body to sense blood pressure, and exist in both arterial and venous structures. An increase in blood pressure causes the vascular wall to stretch, and a decrease in blood pressure causes the vascular wall to return to its original size. Such a cycle is repeated with each beat of the heart. Because baroreceptors 40 are located within the arterial wall, they are able to sense deformation of the adjacent tissue, which is indicative of a change in blood pressure.

Figure 2B:
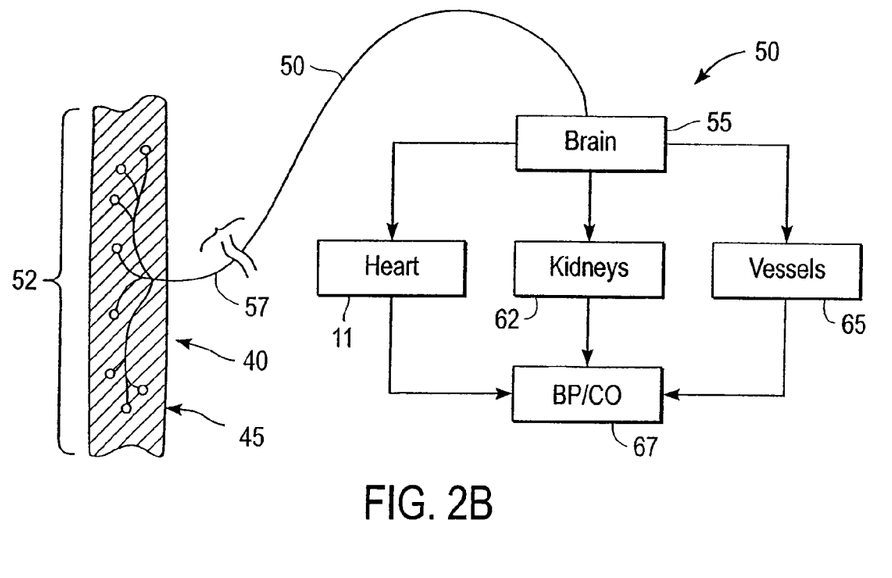
FIG. 2B is a schematic illustration of baroreceptors within the vascular wall, and a schematic flow chart of the baroreflex system.

FIG. 2B is a schematic illustration of baroreceptors 40 within a generic vascular wall 45 and showing the interaction with the baroreflex system, denoted schematically as 50. The baroreceptors 40 located in the right carotid sinus 35, the left carotid sinus, and the aortic arch 15 play the most significant role in sensing blood pressure that affects baroreflex system 50, which is now described in more detail. Specifically, baroreceptors 40 are profusely distributed within the vascular walls 45 of the major arteries discussed previously, and generally form an arbor 52. Baroreceptor arbor 52 comprises a plurality of baroreceptors 40, each of which transmits baroreceptor signals to the brain 55 via a nerve 57. Baroreceptors 40 are so profusely distributed and arborized within the vascular wall 45 that discrete baroreceptor arbors 52 are not readily discernable. To this end, those skilled in the art will appreciate that baroreceptors 40 shown in FIG. 2B are primarily schematic for purposes of illustration and discussion.

Baroreceptor signals are used to activate a number of body systems which collectively may be referred to as baroreflex system 50. Baroreceptors 40 are connected to the brain 55 via the nervous system 60. Thus, the brain 55 is able to detect changes in blood pressure, which is indicative of cardiac output. If cardiac output is insufficient to meet demand (i.e., the heart 12 is unable to pump sufficient blood), baroreflex system 50 activates a number of body systems, including the heart 12, kidneys 62, vessels 65, and other organs/tissues. Such activation of baroreflex system 50 generally corresponds to an increase in neurohormonal activity. Specifically, baroreflex system 50 initiates a neurohormonal sequence that signals the heart 12 to increase heart rate and increase contraction force in order to increase cardiac output, signals the kidneys 62 to increase blood volume by retaining sodium and water, and signals the vessels 65 to constrict to elevate blood pressure. The cardiac, renal and vascular responses increase blood pressure and cardiac output (denoted schematically at 67), and thus increase the workload of the heart 12. In a patient with heart failure, this further accelerates myocardial damage and exacerbates the heart failure state.

System Overview

To address the problems of hypertension, heart failure, other cardiovascular disorders, and renal disorders, the present invention provides techniques by which baroreflex system 50 is activated to reduce excessive blood pressure, autonomic nervous system activity, and neurohormonal activation. In particular, the present invention provides a number of techniques by which baroreceptors 40 and/or nerve fibers that carry signals from the baroreceptors to the brain may be activated, thereby indicating an increase in blood pressure and signaling the brain 55 to reduce the body's blood pressure and level of sympathetic nervous system and neurohormonal activation, and increase parasypathetic nervous system activation, thus having a beneficial effect on the cardiovascular system and other body systems.

Figure 3:
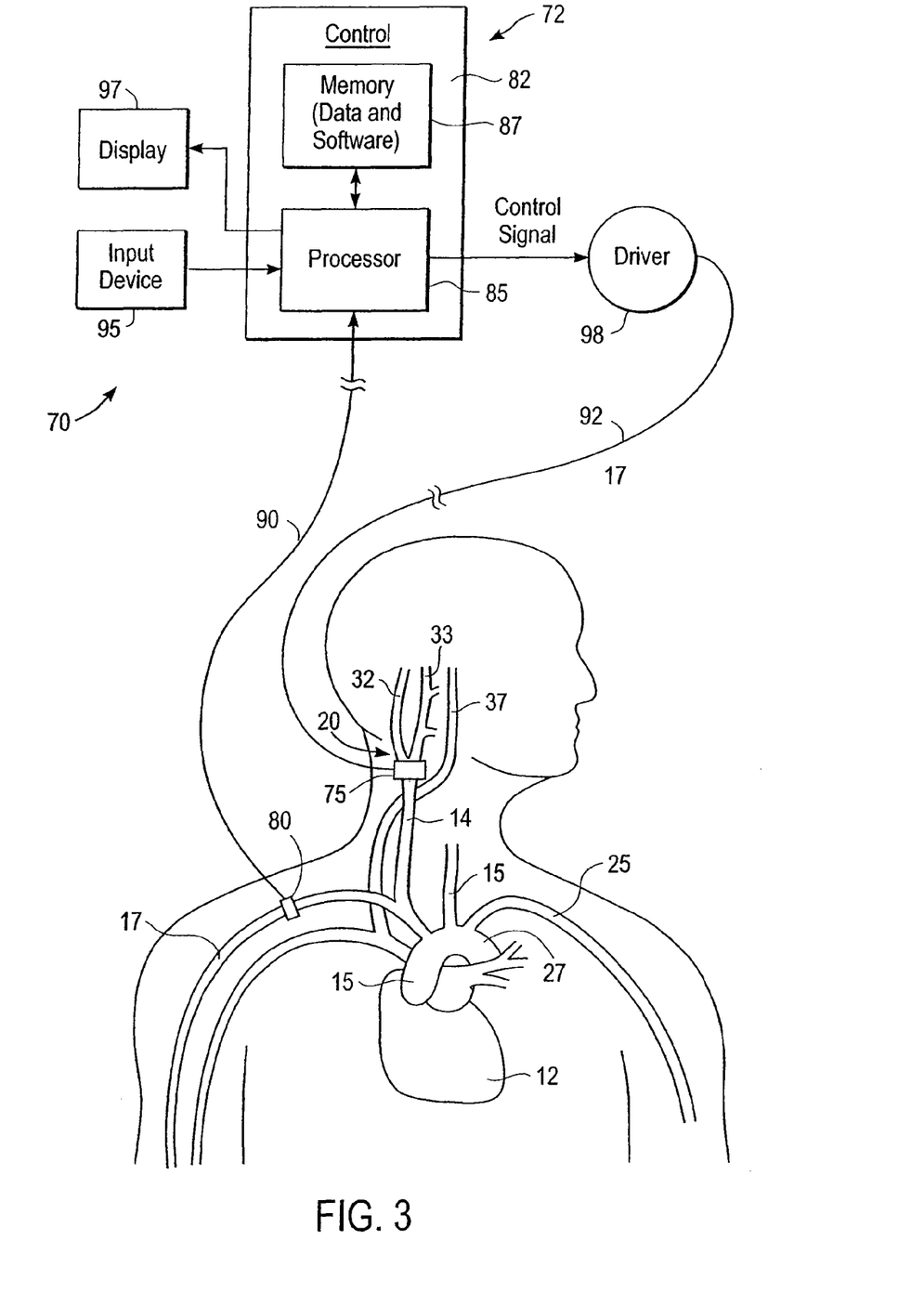
FIG. 3 is a schematic illustration of a baroreflex activation system applied to a human subject according to an embodiment of the present invention.

FIG. 3 is a schematic illustration of a baroreflex activation system 70 applied to a human subject according to an embodiment of the present invention. The human subject may be the person shown in FIG. 1, and corresponding reference numbers are used. In brief, baroreflex activation system 70 includes a control system 72, a baroreflex activation device 75, and an optional sensor 80, which generally operate in the following manner. Sensor 80 optionally senses and/or monitors a parameter (e.g., cardiovascular function) indicative of the need to modify the baroreflex system and generates a signal indicative of the parameter. In some embodiments (not shown), sensor 80 may be incorporated into the structure of baroreflex activation device 75.

Control system 72 generates a control signal that activates, deactivates, or otherwise modulates baroreflex activation device 75. Typically, activation of baroreflex activation device 75 results in activation of baroreceptors 40 and/or nerve fibers that carry signals from the baroreceptor to the brain. Alternatively, deactivation or modulation of baroreflex activation device 75 may cause or modify activation of baroreceptors 40 and/or nerve fibers that carry signals from the baroreceptor to the brain. Control system 72 may generate the control signal according to a predetermined schedule or in response to human action.

For embodiments using optional sensor 80, the control system can generate the control signal as a function of the received sensor signal. This could be independent of a predetermined schedule, or as an adjunct to the schedule. For example, if sensor 80 were to detect a parameter indicative of the need to modify the baroreflex system activity (e.g., excessive blood pressure), control system 72 would cause the control signal to modulate (e.g., activate and/or increase) baroreflex activation device 75, thereby inducing a signal from baroreceptor 40 and/or nerve fibers near the baroreceptor to the brain that is perceived by the brain 55 to be apparent excessive blood pressure. When sensor 80 detected a parameter indicative of normal body function (e.g., normal blood pressure), control system 72 would cause the control signal to modulate (e.g., deactivate and/or decrease) baroreflex activation device 75. The sensor and control system could also be used to control timing of the delivery of the therapy, for example being R-wave triggered, and/or they could also dictate the timing or intensity of the therapy relative to a respiratory cycle. The sensor could also determine the sidedness of the therapy (for example in the presence of AF versus Normal Sinus Rhythm.

By way of example, control system 72 includes a control block 82 comprising a processor 85 and a memory 87. Control system 72 is connected to sensor 80 by way of a sensor cable 90. Control system 72 is also connected to baroreflex activation device 75 by way of a control cable 92. Thus, control system 72 receives a sensor signal from sensor 80 by way of sensor cable 90, and transmits a control signal to baroreflex activation device 75 by way of control cable 92. Control system 72 is also typically provided with an input device 95 and an output device or display 97. Some embodiments generate a control signal that includes trains of short pulses. While the embodiments are not limited to any particular circuitry for generating such pulses, it is noted that a suitable form of pulse generator could include one or more switches, such as field-effect transistor (FET) switches, controlled by processor 85 to connect one or more programmable voltage power supplies to the output.

System components 72/75/80 may be directly linked via cables 90/92 or by indirect means such as RF signal transceivers, ultrasonic transceivers, or galvanic couplings. Examples of such indirect interconnection devices are disclosed in U.S. Pat. No. 4,987,897 to Funke and U.S. Pat. No. 5,113,859 to Funke, the entire disclosures of which are incorporated herein by reference. In some instances, control system 72 includes a driver 98 to provide the desired power mode for baroreflex activation device 75. For example, the driver 98 may comprise a power amplifier or the like and cable 92 may comprise electrical lead(s). In other instances, driver 98 may not be necessary, particularly if processor 85 generates a sufficiently strong electrical signal for low level electrical actuation of baroreflex activation device 75.

Representative Baroreflex Activation Devices

Baroreflex activation device 75 may comprise a wide variety of devices that utilize mechanical, electrical, thermal, chemical, biological, or other means to activate baroreceptors 40 and/or nerve fibers which carry signals from the baroreceptors to the brain. Thus, when control system 72 generates a control signal to modulate (e.g., activate) baroreflex activation device 75, this induces a signal from baroreceptor 40 and/or nerve fibers that carry signals from the baroreceptor to the brain that is perceived by the brain 55 to be apparent excessive blood pressure, and the baroreflex system operates to lower the blood pressure.

Baroreflex activation device 75 may directly activate one or more baroreceptors 40 by changing the electrical potential across baroreceptors 40. It is also possible that changing the electrical potential might indirectly change the thermal or chemical potential across the tissue surrounding baroreceptors 40 and/or otherwise may cause the surrounding tissue to stretch or otherwise deform, thus mechanically activating baroreceptors 40 and/or nerve fibers that carry signals from the baroreceptor to the brain. Thus, baroreflex activation device 75 activates baroreceptors 40 and/or nerve fibers that carry signals from the baroreceptor to the brain electrically, optionally in combination with mechanical, thermal, chemical, biological or other co-activation. However, it is generally contemplated that the control signal that energizes baroreflex activation device 75 will be an electrical signal. One suitable form of baroreflex activation device is a bipolar electrode structure having two leads for applying a voltage across a baroreceptor and/or nerve fibers that carry signals from the baroreceptor to the brain.

Baroreflex activation device 75 is suitable for implantation, and is preferably implanted using a minimally invasive percutaneous transluminal approach and/or a minimally invasive surgical approach. Baroreflex activation device 75 may be positioned anywhere that baroreceptors 40 affecting baroreflex system 50 are numerous, such as in the heart 12, in the aortic arch 15, in the common carotid arteries 20/22 near the carotid sinus 35, in the subclavian arteries 17/25, in the brachiocephalic artery 30, in the veins (not shown), or in the cardiopulmonary region (not shown). Baroreflex activation device 75 may be implanted such that it is positioned immediately adjacent baroreceptors 40 and/or nerve fibers that carry signals from the baroreceptor to the brain. Alternatively, baroreflex activation device 75 may be outside the body such that the device is positioned a short distance from but proximate to baroreceptors 40 and/or nerve fibers that carry signals from the baroreceptor to the brain. Preferably, baroreflex activation device 75 is implanted near the right carotid sinus 35 and/or the left carotid sinus (near the bifurcation of the common carotid artery) and/or the aortic arch 15, where baroreceptors 40 and/or nerve fibers that carry signals from the baroreceptor to the brain have a significant impact on baroreflex system 50.

For purposes of illustration only, the present invention is described with reference to baroreflex activation device 75 positioned near the carotid sinus 35. Furthermore, for clarity, FIG. 3 shows a single baroreflex activation device 75. However, it is believed that advantages can be achieved by providing two or more baroreflex activation devices, and energizing them in a synchronous, sequential, or alternating manner. For example, similar devices could be positioned in both carotid sinus regions (or other regions), and driven alternately. This will be described in greater detail below.

Representative Sensors

While sensor 80 is optional, and embodiments of the invention can operate without using such a sensor, the sensor is a useful feature, and several representative types will be discussed. Sensor 80 may comprise any suitable device that measures or monitors a parameter indicative of the need to modify the activity of the baroreflex system. For example, sensor 80 may comprise a physiologic transducer or gauge that measures ECG, blood pressure (systolic, diastolic, average or pulse pressure), blood volumetric flow rate, blood flow velocity, blood pH, oxygen or carbon dioxide content, mixed venous oxygen saturation ($SVO_2$), vasoactivity, nerve activity, tissue activity, or tissue or blood composition. Examples of suitable transducers or gauges for sensor 80 include ECG electrodes, a piezoelectric pressure transducer, an ultrasonic flow velocity transducer, an ultrasonic volumetric flow rate transducer, a thermodilution flow velocity transducer, a capacitive pressure transducer, a membrane pH electrode, an optical detector ($SVO_2$) or a strain gage. Although only one sensor 80 is shown, multiple sensors 80 of the same or different type at the same or different locations may be utilized.

An example of an implantable blood pressure measurement device that may be disposed about a blood vessel is disclosed in U.S. Pat. No. 6,106,477 to Miesel et al., the entire disclosure of which is incorporated herein by reference. An example of a subcutaneous ECG monitor is available from Medtronic under the trade name REVEAL ILR and is disclosed in PCT Publication No. WO 98/02209, the entire disclosure of which is incorporated herein by reference. Other examples are disclosed in U.S. Pat. Nos. 5,987,352 and 5,331,966, the entire disclosures of which are incorporated herein by reference. Examples of devices and methods for measuring absolute blood pressure utilizing an ambient pressure reference are disclosed in U.S. Pat. No. 5,810,735 to Halperin et al., U.S. Pat. No. 5,904,708 to Goedeke, and PCT Publication No. WO 00/16686 to Brockway et al., the entire disclosures of which are incorporated herein by reference. Sensor 80 described herein may take the form of any of these devices or other devices that generally serve the same purpose.

Sensor 80 is preferably positioned in a chamber of the heart 12, or in/on a major artery such as the aortic arch 15, a common carotid artery 20/22, a subclavian artery 17/25 or the brachiocephalic artery 30, such that the parameter of interest may be readily ascertained. Sensor 80 may be disposed inside the body such as in or on an artery, a vein or a nerve (e.g., vagus nerve), or disposed outside the body, depending on the type of transducer or gauge utilized. Sensor 80 may be separate from baroreflex activation device 75 or combined therewith. For purposes of illustration only, sensor 80 is shown positioned on the right subclavian artery 17.

Control System

Memory 87 may contain data related to the sensor signal, the control signal, and/or values and commands provided by input device 95. Memory 87 may also include software containing one or more algorithms defining one or more functions or relationships between the control signal and the sensor signal. The algorithm may dictate activation or deactivation control signals depending on the sensor signal or a mathematical derivative thereof. The algorithm may dictate an activation or deactivation control signal when the sensor signal falls below a lower predetermined threshold value, rises above an upper predetermined threshold value or when the sensor signal indicates a specific physiologic event. The algorithm may dynamically alter the threshold value as determined by the sensor input values.

Control system 72 may operate as a closed loop utilizing feedback from sensor 80, or other sensors, such as heart rate sensors which may be incorporated on the electrode assembly, or as an open loop utilizing reprogramming commands received by input device 95. The closed loop operation of control system 72 preferably utilizes some feedback from sensor 80, but may also operate in an open loop mode without feedback. Programming commands received by input device 95 may directly influence the control signal, the output activation parameters, or may alter the software and related algorithms contained in memory 87. The treating physician and/or patient may provide commands to input device 95. Display 97 may be used to view the sensor signal, control signal and/or the software/data contained in memory 87.

The control signal generated by control system 72 may be continuous, periodic, alternating, episodic, or a combination thereof, as dictated by an algorithm contained in memory 87. Continuous control signals include a constant pulse, a constant train of pulses, a triggered pulse and a triggered train of pulses. Examples of periodic control signals include each of the continuous control signals described above which have a designated start time (e.g., beginning of each period as designated by minutes, hours, or days in combinations of) and a designated duration (e.g., seconds, minutes, hours, or days in combinations of). Examples of alternating control signals include each of the continuous control signals as described above which alternate between the right and left output channels. Examples of episodic control signals include each of the continuous control signals described above which are triggered by an episode (e.g., activation by the physician/patient, an increase/decrease in blood pressure above a certain threshold, heart rate above/below certain levels, respiration, etc.).

Stimulus Regimen Overview

The stimulus regimen governed by control system 72 may be selected to promote long term efficacy. It is possible that uninterrupted or otherwise unchanging activation of baroreceptors 40 and/or nerve fibers that carry signals from the baroreceptor to the brain may result in the baroreceptors and/or the baroreflex system becoming less responsive over time, thereby diminishing the long term effectiveness of the therapy. Therefore, the stimulus regimen maybe selected to activate, deactivate or otherwise modulate baroreflex activation device 75 in such a way that therapeutic efficacy is maintained for months, preferably for years.

In addition to maintaining therapeutic efficacy over time, the stimulus regimens of the present invention may be selected to reduce the power requirement/consumption of control system 72. As will be described in more detail below, the stimulus regimen may dictate that baroreflex activation device 75 be initially activated at a relatively higher energy and/or power level, and subsequently activated at a relatively lower energy and/or power level. The first level attains the desired initial therapeutic affect, and the second (lower) level sustains the desired therapeutic affect long term. By reducing the energy and/or power levels after the desired therapeutic affect is initially attained, the energy required or consumed by baroreflex activation device 75 is also reduced long term. This may correlate into systems having greater longevity and/or reduced size (due to reductions in the size of the power supply and associated components).

A first general approach for a stimulus regimen which promotes long term efficacy and reduces power requirements/ consumption involves generating a control signal to cause baroreflex activation device 75 to have a first output level of relatively higher energy and/or power, and subsequently changing the control signal to cause baroreflex activation device 75 to have a second output level of relatively lower energy and/or power. The first output level may be selected and maintained for sufficient time to attain the desired initial affect (e.g., reduced heart rate and/or blood pressure), after which the output level may be reduced to the second level for sufficient time to sustain the desired affect for the desired period of time.

Details of Baroreflex Activation Control Signal to Effect Desired Stimulus Regimens Baroreflex activation is effected by applying an electrical control signal to a baroreflex activation device, which can apply one or more of many different kinds of stimulus to one or more baroreceptors and/or nerve fibers that carry signals from the baroreceptors to the brain in the vicinity of the activation device. For example, the baroreceptor and/or nerve fibers that carry signals from the baroreceptor to the brain can be stimulated mechanically, electrically, magnetically, thermally, optically, chemically, or biologically to induce the desired baroreceptor signal.

In electrical activation embodiments using a non-modulated signal, the output (power or energy) level of baroreflex activation device 75 may be changed by changing the voltage, current, signal duration and/or frequency. The output signal of baroreflex activation device 75 may be, for example, constant current or constant voltage. In a number of specific embodiments, the control signal includes a train of relatively narrow pulses, and the electrical power applied to the baroreflex activation device can be varied by controlling one or more of the pulse characteristics. Such pulse characteristics include, but are not limited to, amplitude, pulse width (or duration), pulse frequency (or inversely, the interval between the starts of successive pulses), pulse waveform (e.g., square, triangular, sinusoidal, etc.), pulse polarity (for bipolar electrodes), and pulse phase (monophasic, biphasic).

Figure 4:
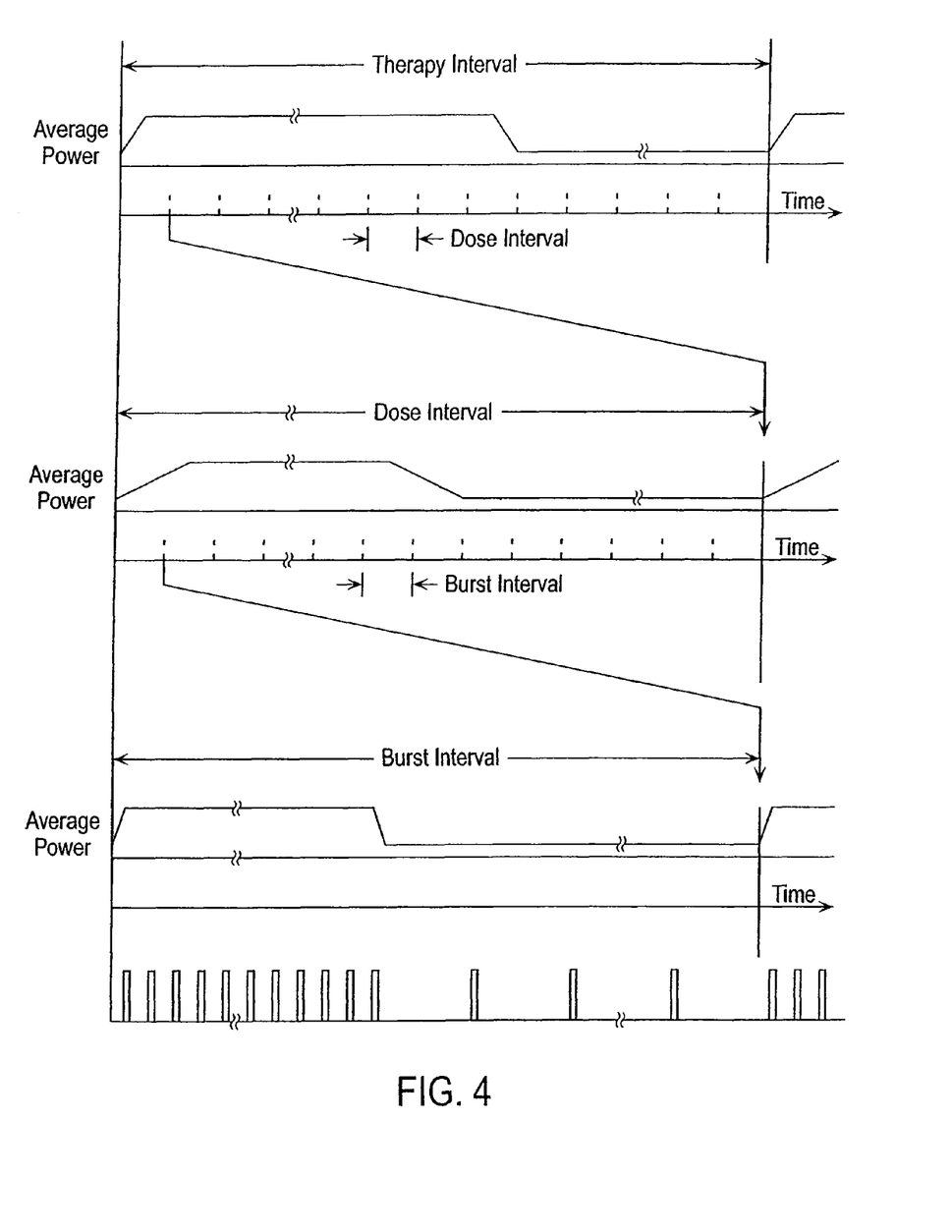
FIG. 4 is a set of schematic timing diagrams of a representative baroreflex activation device control signal according to an embodiment of the present invention.

FIG. 4 is a set of schematic timing diagrams of a representative baroreflex activation device control signal according to an embodiment of the present invention. FIG. 4 illustrates a hierarchical organization of the control signal on progressively shorter time scales. Further, the vertical axis is labeled in terms of "average power." Electrical power, as normally used, means an amount of energy per unit time, and the average power over a time interval represents the instantaneous power averaged (or integrated) over that interval. The concept is refined at the different time scales, as will now be described.

FIG. 4 is divided into three sections, corresponding to a hierarchy of time intervals that are referred to as "therapy intervals," "dose intervals," and "burst intervals." As can be seen in the top (first) section of this particular hierarchy, the therapy interval is divided up into a plurality of dose intervals, one of which is shown on the expanded scale of the middle (second) section. As can be seen in the middle section, each dose interval is itself divided into burst intervals, one of which is on the expanded scale of the bottom (third) section. FIG. 4 also shows the average power over each interval according to this specific embodiment.

Although the invention is not limited to specific pulse widths, amplitudes, and frequencies, it is convenient to set forth some representative orders of magnitude. For example, in different embodiments, the activation timing can be considered to characterized by a time hierarchy defined by therapy intervals on the order of minutes to several hours, dose intervals on the order of one to several minutes, and burst intervals on the order of a second (the interval between heartbeats). Within a burst interval, pulses having widths (programmable in some implementations) on the order of half a millisecond may be generated at pulse rates on the order of 1-200 pulses per second, but preferably 5-200 pulses per second. More broadly speaking, however, the therapy interval can be on the order of a minute to hours or days (or even of indefinite duration—i.e., continuous), and the dose duration can be on the order of a second to several hours.

In this embodiment, the therapy interval has an average power profile that is characterized by a first portion characterized by a first average power level (the first therapy portion average power) and a second portion characterized by a second average power level (the second therapy portion average power). Gradual transitions between the two average power levels are shown schematically as linear ramps, but other transitions are possible. The transitions could also be polygonal, or could be smooth transitions (as opposed to merely continuous as shown). Indeed, the transitions could be step functions as well, although more gradual transitions are generally preferred.

In an analogous manner, the dose and burst intervals are shown as having similar average power profiles. Thus the dose interval is shown as having an average power profile that is characterized by a first portion characterized by a first average power level (the first dose portion average power) and a second portion characterized by a second average power level (the second dose portion average power). Similarly, the burst interval is shown as having an average power profile that is characterized by a first portion characterized by a first average power level (the first burst portion average power) and a second portion characterized by a second average power level (the second burst portion average power).

For definiteness, FIG. 4 shows the first average power level as higher than the second, but that is to some extent a function of where one draws the boundaries of the intervals. For example, if the boundaries of the intervals were drawn at the points where the average power was decreasing, one could equally well say that each interval had a first portion with an average power that was lower than the average power in the second portion of the interval. FIG. 4 is general in that the lower average power is shown as non-zero, although in some embodiments, the lower average power could be zero.

Within the context of this time hierarchy, the notion of average power will be discussed. In short, averaging is performed over an interval that is relevant to the context of the time scale of the timing diagram. For the burst interval, the average is computed over a few or several pulses. Similarly, within the context of the dose interval, averaging is performed over one or more burst intervals. In the case of the therapy interval, the averaging is performed over one or more dose intervals.

It should be recognized that the time profiles for therapy intervals, dose intervals, and burst intervals, while interdependent, are also to a certain extent independent. Thus, for example, it is not necessary for the dose intervals to have an average power (averaged over burst intervals) that varies with time. Rather, the dose intervals for the first portion of the therapy interval could have constant average power at one level, and the dose intervals for the second portion of the therapy interval could have constant average power at a different level. Indeed, to the extent that there is no particular time structure over each dose interval, the notion of dose interval becomes somewhat irrelevant in many embodiments.

In the example shown, the change in average power over the burst interval is provided by generating pulses with the same amplitude and width, but at different frequencies. The ratio of pulse frequencies is shown as a factor of 4, with a concomitant factor of 4 in average power. It can be seen from the figure that the instantaneous power is zero most of the time. It should be noted that a statement that the average power for the first portion of the interval is higher than the average power for the second portion of the interval does not imply that the total energy for the first portion is higher than the total energy for the second portion unless the first portion is at least as long as the second portion. FIG. 4 is drawn generally, so that the first portion of each interval may be longer or shorter than the second portion (note broken lines on the timing diagrams).

There are many possible ways to impose a desired time profile of average power on the baroreflex activation device control signal. Consider, for example, an embodiment where it is desired to have the varying power during each of the therapy, dose, and burst intervals (as specifically shown in FIG. 4). Assuming that the basic electrical signal will be a series of pulses, the time-dependent power over the burst can be achieved by varying one or more of the pulse characteristics over each burst interval. The time-dependent power over the dose intervals can be achieved by superimposing an appropriate variation of one or more of the same or different pulse characteristics. For example, the variation over each burst interval can be achieved by varying the pulse frequency, and the variation over each dose interval can be achieved by superimposing a variation in pulse width or amplitude. Similarly, the variation over the therapy interval can be achieved by superimposing an appropriate variation of one or more of the same or different pulse characteristics.

As alluded to above, it is often desirable to activate baroreceptors and/or nerve fibers that carry signals from the baroreceptor to the brain at multiple sites, such as baroreceptors and/or nerve fibers that carry signals from the baroreceptor to the brain at both of the carotid sinuses. Thus the control signal may need to be applied to two or more baroreflex activation devices. It is preferred that only one baroreflex activation device 75 be energized at any given moment. One reason is to avoid possible ill effects in the event that an electrode or electrode lead failed. An impedance mismatch can lead to cross-coupling of current. For example, if one lead of a bipolar electrode broke, the signal would try to find a return path, and if the electrode on the other side of the neck were being energized at the same time, that return path would be across the subject's neck. Accordingly, it is desired to interleave the application of energy to the two (or more) baroreflex activation devices, and the signals can be interleaved at different levels.

A conceptually different use of multiple baroreflex activation devices 75 is where the devices are located near each other, say as a closely spaced array of such devices. In such a case it may still be desirable to energize only one of the devices in the array at a time, even though the risk of stray currents across the subject's neck is no longer present.

Figure 5:
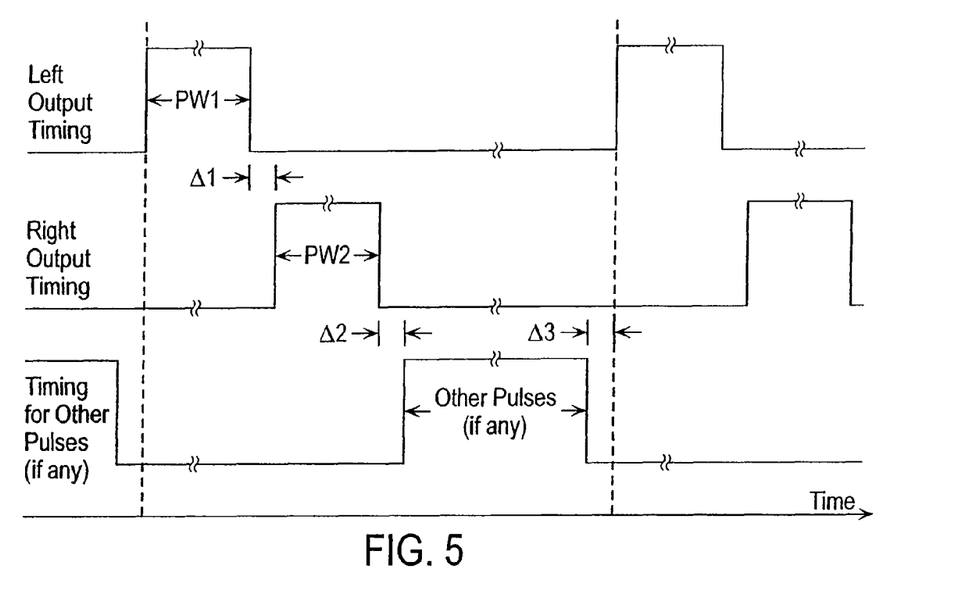
FIG. 5 is a timing diagram showing aspects of interleaving control signals for two baroreflex activation devices at a pulse level according to an embodiment of the present invention.

FIG. 5 is a timing diagram showing interleaving control signals for two baroreflex activation devices at the pulse level. That is, individual pulses are alternated between the two baroreflex activation devices, arbitrarily designated left and right. Two pulses in each pulse train are shown, with the separation between successive pulses in each channel corresponding to those in FIG. 4. The pulses for the two baroreflex activation devices have respective pulse widths PW1 and PW2, which are likely to be equal, but need not be.

As noted above, it is desired that the two baroreflex activation devices not be energized simultaneously (at least where the two baroreflex activation devices are widely separated). To this end, a delay Δ1 is imposed between the end of the pulse in the left channel and the beginning of the pulse in the right channel, and a delay Δ2 is imposed between the end of the pulse in the right channel and the beginning of any subsequent pulse (e.g., where the control signal interleaves pulses among three or more baroreflex activation devices). This timing ensures that the activation energy is delivered into the desired region in the subject, independent of tissue impedance effects.

The figure is drawn schematically as showing a third timing interval for "Other Pulses (if any)" to represent a time interval during which pulses for additional (beyond two) baroreflex activation devices could be energized. A delay Δ3 is imposed between the end of the last pulse and the beginning of the pulse in the left channel. For the special case of two-way interleaving of the baroreflex activation pulses, the third timing interval would be devoid of pulses, and delay Δ3 and the third timing interval could just be considered the OFF time in the sequence. As a practical matter, even where there are only two pulses in each sequence, there is likely to be significant interval (i.e., longer than PW1 and PW2) after the end of the pulse in the right channel before a pulse is generated for the left channel.

In a representative embodiment, where a representative pulse frequency is on the order of 20 Hz (Hertz), corresponding to a pulse every 50 ms (milliseconds), the pulse widths PW1 and PW2 are programmable, but typically less than 1 ms, Δ1 is 30-250 μs (microseconds), Δ2 and Δ3 are at least 30 μs. The charge balance interval CBW is set at 8±2 ms. These numbers are, as mentioned above, exemplary and are by no means critical. A nominal heart rate is 1-1.2 Hz (burst interval of 0.83-1 second), so a representative burst interval might comprise 6-8 pulses at 20 Hz over the first 250-350 ms followed by no pulses or pulses at a lower frequency over the remainder of the burst interval.

As noted above, if pulses are applied to an array of two or more closely spaced baroreflex activation devices, it may still be desired that there be a separation of the pulses. However, it may also be desired that the pulses to the different baroreflex activation devices in the array be phased (i.e., commence at different times, with overlap).

Figure 6:
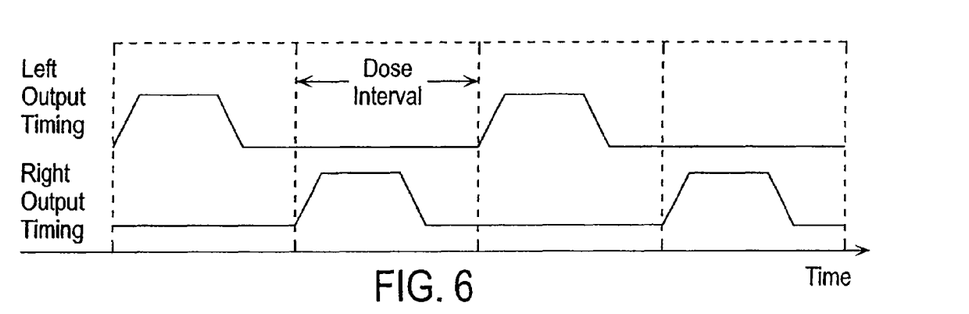
FIG. 6 is a timing diagram showing aspects of interleaving control signals for two baroreflex activation devices at a dose level according to an embodiment of the present invention.

FIG. 6 is a timing diagram showing interleaving control signals for two baroreflex activation devices at the dose level. Rather than interleaving the individual pulses between the two baroreflex activation devices, it is possible to direct alternate doses to the left and right channels. It is also possible to direct alternate bursts to the left and right channels (FIG. 6 would show this if the legend "Dose Interval" were relabeled "Burst Interval"). It is also possible to interleave at the therapy level (FIG. 6 would show this if the legend "Dose Interval" were relabeled "Therapy Interval"). The considerations for interleaving at the dose or burst level are different than for interleaving at the pulse level. Interleaving at the dose and/or burst level is believed to promote efficacy.

Figure 7:
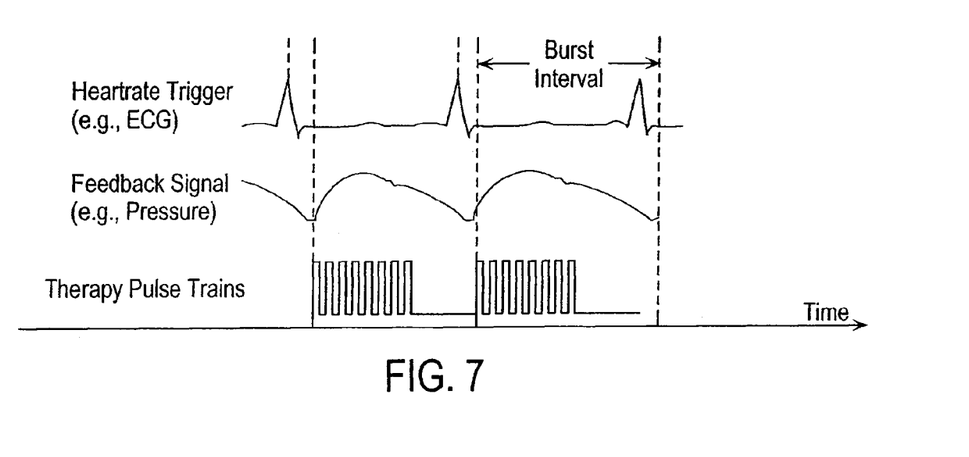
FIG. 7 is a timing diagram showing the timing of a control signal for a baroreflex activation device triggered by a heartbeat or blood pressure pulse according to an embodiment of the present invention.

FIG. 7 is a timing diagram showing the timing of a control signal for a baroreflex activation device triggered by a heartbeat or blood pressure signal. FIG. 7 shows the heartbeat signal such as an electrocardiogram (ECG, e.g., R-wave) signal, as well as an arterial pressure signal. In the particular implementation shown, the pulse trains are triggered by minima in the blood pressure signal. It is noted that the burst intervals are now no longer of fixed length, but vary somewhat according to variations in the subject's heart rate.

It is also possible to trigger the pulse trains on the basis of other timing signals and events (including those that are not physiologic in origin). FIG. 7 shows but one example of the relative timing, and it will be understood that the triggering event may be changed and/or the delay from the triggering event may be changed. The various possible triggering signals and events may be used singly or in any desired combinations, depending on the circumstances. A number of possible alternative and/or adjunct trigger signals and events will now be discussed.

A slow physiologic event such as the subject's respiration can be used for timing, as can time-of-day events such as signals provided by sensors detecting whether the subject is resting or awake, or even an internal time of day clock. It is also contemplated that one or more of these various signals or events can be used in a closed loop system to modulate the baroreflex activation parameters, and further that the subject can intervene to modulate one or more of the parameters.

CONCLUSION

In conclusion, it can be seen that the present invention provides great flexibility in the timing of control signals for baroreflex activation. While the above is a complete description of specific embodiments of the invention, the above description should not be taken as limiting the scope of the invention as defined by the claims.

What is claimed is:

1. A method of treating a patient with a baroreflex activation device, the method comprising:
    establishing a series of therapy intervals;
    establishing a plurality of burst intervals during at least one of the therapy intervals;
    wherein the burst intervals are commensurate with an interval between heartbeats of the patient;
    generating an electrical output signal, based on the series of therapy intervals, characterized in that electrical power applied to the activation device has a time dependence;
    wherein at least one of the therapy intervals has a first portion characterized by an average electrical power, referred to as a first therapy portion average power, and a second portion characterized by an average electrical power, referred to as a second therapy portion average power, the first therapy portion average power being different from the second therapy portion average power, and wherein at least one of the burst intervals has a first portion characterized by an average electrical power, referred to as a first burst portion average power, and a second portion characterized by an average electrical power, referred to as a second burst portion average power, the first burst portion average power being different from the second burst portion average power.

2. The method of claim 1 wherein generating the electrical output signal comprises generating electrical pulses having one or more pulse characteristics chosen to provide said time dependence of electrical power applied to the activation device.

3. The method of claim 2 wherein said pulse characteristics include one or more of pulse amplitude, pulse width, pulse frequency, pulse separation, pulse waveform, pulse polarity, and pulse phase.

* * * * *